United States Patent
Maekawa et al.

[11] Patent Number: 5,769,076
[45] Date of Patent: Jun. 23, 1998

[54] NON-INVASIVE BLOOD ANALYZER AND METHOD USING THE SAME

[75] Inventors: Yasunori Maekawa; Kaoru Asano; Yasuhiro Kochi; Ken Ishihara, all of Hyogo, Japan

[73] Assignee: TOA Medical Electronics Co., Ltd., Hyogo, Japan

[21] Appl. No.: 641,828

[22] Filed: May 2, 1996

[30] Foreign Application Priority Data

May 2, 1995 [JP] Japan ..................................... 7-108723

[51] Int. Cl.$^6$ ...................................................... A61B 5/00
[52] U.S. Cl. ........................... 128/633; 128/664; 128/665
[58] Field of Search ..................................... 128/633, 637, 128/664, 665; 356/39

[56] References Cited

U.S. PATENT DOCUMENTS

| | | |
|---|---|---|
| 4,998,533 | 3/1991 | Winkelman . |
| 5,240,006 | 8/1993 | Fujii et al. .............................. 128/665 |
| 5,279,297 | 1/1994 | Wilson et al. ........................... 128/633 |
| 5,394,199 | 2/1995 | Flower ..................................... 128/633 |
| 5,437,274 | 8/1995 | Khoobehi et al. ...................... 128/664 |

FOREIGN PATENT DOCUMENTS 4-161915   6/1992   Japan .

*Primary Examiner*—Jennifer Bahr
*Assistant Examiner*—Eric F. Winakur

[57] ABSTRACT

A non-invasive blood analyzer contains a light applicator for illuminating a detection region under the skin of a living body including a blood vessel; a camera for capturing an image of the illuminated detection region; an analyzer for processing the captured image and analyzing at least a component of blood in the blood vessel; a transparent plate; and a support for supporting the transparent plate and contacting the transparent plate closely with the skin over the detection region. The light applicator and the camera are constructed to illuminate the detection region and capture the image of the detection region through the transparent plate. Further, a drive controller is included for driving the support to move the transparent plate contacted closely with the skin in order to adjust the detection region to thereby compensate for any change in position of the blood vessel.

19 Claims, 12 Drawing Sheets

5,769,076

NON-INVASIVE BLOOD ANALYZER AND METHOD USING THE SAME

BACKGROUND OF THE INVENTION

1. Field of the Invention

The present invention relates to an apparatus and method for analyzing blood in a non-invasive manner, and more particularly to an apparatus and method for analyzing blood components necessary for a hematology test by optically measuring blood flowing through blood vessels in a living body.

2. Description of Related Art

Analysis of blood components is extremely important for the diagnosis of diseases and the treatment thereof. Generally, such a hematology test involves collecting blood from a living body to analyze a sample thereof with an analyzer. However, the collection of blood from the living body causes considerable pain to the living body. Also, since the collected blood is usually transported, before analysis, to an inspection room where an analyzing apparatus is placed, it is impossible to conduct a real-time hematology test during diagnosis. Moreover, the above method is always accompanied by the fear that a needle for collecting blood used for a person infected with an infectious disease such as hepatitis and AIDS might be accidentally used.

Thus, a demand has been made for many years that an apparatus be developed that allows practitioners to perform a blood test in a non-invasive manner. When such a blood analyzer is installed beside the bed on which the living body lies, a practitioner can monitor real-time conditions thereof on the spot without difficulty.

Examples of the known prior art relating to such apparatus include a video microscope which applies light to an observation site on a skin surface of a living body to capture at regular intervals video images thereof (static images) at a shutter speed of about one thousandth of a second, identifies a discontinuous point in the blood stream on the static images and calculates the speed of the blood stream from the positions of the discontinuous point on the static images; and an analyzer having a video camera equipped with a high-speed shutter which captures images of red blood cells in the conjunctival capillary vessels in an eyeball (see Japanese Unexamined Patent Publication No. Hei4(1992)-161915 and U.S. Pat. No. 4,998,533).

Such a conventional blood analyzer can analyze by imaging a microvascular vessel such as a capillary vessel and arteriole near the skin surface. However, the analyzer disadvantageously cannot obtain an accurate result due to a bio-rheological factor such as deformation of red cells in a capillary vessel of a smaller diameter than that of a red blood cell.

For obtaining accurate results from an image of a vessel, the analyzer preferably captures an image of a vessel of a larger diameter than that of a capillary vessel, i.e., of a diameter of about 20 $\mu$m. Such a vessel is called an arteriole or venule.

However, when the observation site is a lip, for example, since capillaries, arterioles and venules exist together at intervals of several tens of $\mu$m, a desired vessel must be detected in some way.

Also, since it is impossible to eliminate a subtle move caused by a body movement of a person under test, it is required to shift a region to be imaged following the body movement to obtain a stable detection region.

SUMMARY OF THE INVENTION

The present invention has been conceived in view of the above circumstances, and an object of the invention is to provide a non-invasive blood analyzer which illuminates and captures images through a transparent plate contacted with a skin surface of a living body and which is also capable of shifting a region to be imaged to detect a desired vessel and compensate for a difference in position of the vessel, and a method using the same.

The present invention provides a non-invasive blood analyzer comprising; light application means for illuminating a detection region including a blood vessel having blood flowing therethrough, the detection region being under a skin of a part of a living body; image capturing means for capturing an image of the illuminated detection region; analysis means for processing the captured image and at least analyzing a component of the blood in the blood vessel in the detection region; a transparent plate; support means for supporting the transparent plate and contacting the transparent plate closely with the skin over the detection region, the light application means and the image capturing means being constructed to illuminate the detection region and capture the image of the detection region through the transparent plate; and drive control means for driving the support means to move the transparent plate contacted closely with the skin in order to adjust the detection region.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
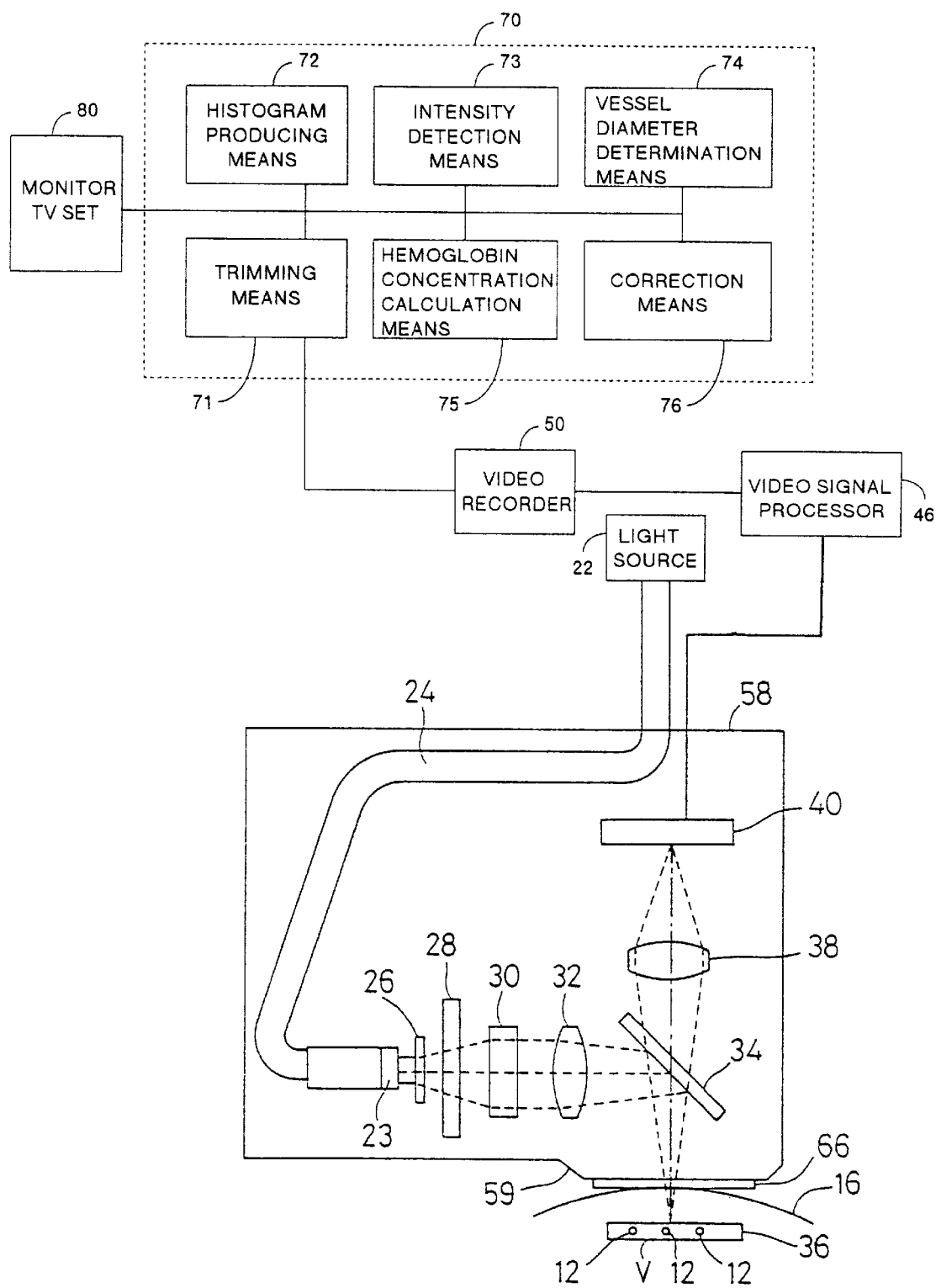
FIG. 1 is a view illustrating the structure of embodiment 1 of the present invention.

The blood analyzer of the present invention is characterized by analyzing blood components of a living body in a non-invasive manner. The living body is preferably that of mammals including human beings.

The detection region refers to a region of the living body including a vessel which is present as it is in the living body, and does not refer to a part of the body surgically taken out of the living body. Obtained data about the blood of an arteriole or venule may be converted to those of a larger vessel such as a medium-sized artery and vein, the main artery and vein, etc.

As a light source of the light application means of the present invention, either a continuous or intermittent light source may be used; the continuous light source that continuously applies light may be a laser, a halogen lamp or a tungsten lamp, and the intermittent light source that applies light intermittently may be a pulse laser (for example, 7000 series manufactured by Spectra-Physics Co., Ltd.) or a flash lamp (for example, DSX series manufactured by Sugawara Laboratories, Inc., Japan).

Preferably, in addition to the above light source, the light application means may further comprise at least one of (1) an optical fiber, (2) a reflector, (3) a lens and (4) a slit to direct the light from the light source right properly to the detection region. The light application means may comprise the above (1) and (2), (1) and (3), (1) and (2) and (3), (1) and (2) and (3) and (4), or (2) and (3) and (4) in combination.

In the above case, a prism may be used in the place of the reflector. In addition, the light application means may comprise a polarizing device to apply polarized light to the detection region.

As the image capturing means of the present invention, a general CCD image sensor may be used, for example.

Further, the image capturing means may comprise at least one of an optical fiber, reflector of each kind, polarizing element, a lens of each kind, prism, slit and filter in its optical system to direct reflected light from the detection region to CCD image sensor. When the reflected light from the detection region is weak, the image capturing means preferably comprises an image intensifier. The image capturing means may optionally comprise a polarizing device for removing unnecessary scattered light components reflected from the detection region.

Further, the image capturing means preferably comprises a video signal processor for supplying a scanning signal to the CCD image sensor and processing an output from each pixel of the CCD image sensor into a video signal, and a VTR, laser disk recorder or other digital or analog signal storing device for storing the video signal.

As the transparent plate contacted with the skin surface of the living body, a glass or plastic sheet may be used, for example.

The analysis device may have a function for determining a diameter of the blood vessel and comparing the diameter with a predetermined value. The drive control device controls the support device to move the transparent plate by a predetermined distance when the diameter is smaller than the predetermined value.

The analysis device may have a function for processing the image and determining a difference in position on repeatedly captured images with respect to the blood vessel. The drive control device controls the support device to move the transparent plate so as to minimize the difference when the difference is determined.

The support means, for example, may include a support plate having a window for receiving the transparent plate.

The support means may include a support plate having a window for receiving the transparent plate, a sliding board to which the support plate is exchangeably attached and/or a support member for slidably supporting the sliding board.

The support means may include a support member for slidably supporting the transparent plate.

The support means may include a support member for slidably supporting the transparent plate and a fixing device for fixing the support member on the living body.

The drive control means may include a bias device for forwardly biasing the transparent plate in a sliding direction and pressing device for backwardly pressing the transparent plate in the sliding direction. Preferably, the bias means contains a spring and the pressing device contains a rod and a motor for linearly moving the rod.

According to the above-described non-invasive blood analyzer, it is preferable to capture images successively by shifting the detection region under the skin by the drive control device, comparing a diameter of each imaged blood vessel with a predetermined value and analyzing a component of the blood contained in the blood vessel when the imaged blood vessel is larger than the predetermined value in diameter.

According to the above-mentioned non-invasive blood analyzer, when images of a blood vessel are captured a plurality of times for analyzing a component of the blood contained in the blood vessel, it is preferable to determine a difference in position on at least two captured images with respect to the blood vessel, move the transparent plate by such a distance that the difference is minimized and then capture a next image of the blood vessel.

When the transparent plate is moved by the drive control device, a part of the living body contacted with the transparent plate is moved due to a frictional force between the contact faces and consequently the detection region captured by the image capturing device is shifted. Since the move is several tens of $\mu$m to several mm at most, the move is not such that the flow of blood is disturbed. However the move is enough to detect a desirable vessel since capillaries, arterioles and venules exist together at intervals of several tens of $\mu$m under the skin of the living body.

For judging whether a vessel in an imaged region is a desirable vessel appropriate for the analysis, the diameter of the vessel, for example, may be determined by analyzing and binarizing the image of the vessel, and then compared with a given value (e.g., 20 $\mu$m).

By obtaining a difference from a standard image by image-processing and then shifting the transparent plate to compensate for the difference, the detection region can be stabilized against an outer disturbance such as a body move, and accurate determination can be obtained. Alternatively, the shift of the transparent plate can be controlled manually.

The present invention will be detailed in conjunction with the preferred embodiments, which are not intended to limit the scope of the present invention.

Embodiment 1

FIG. 1 is a view illustrating the structure of embodiment 1 of the non-invasive blood analyzer of the present invention. The analyzer, if divided broadly into two large categories, is constituted of a probe 58 and an analysis device 70.

A light beam emitted by a light source of a halogen lamp 22 illuminates a diffuser 26 via an optical fiber 24 and filter 23. The light beam is diffused by the diffuser 26, and illuminates a plate 28 uniformly. The plate 28 acts substantially as plane illuminant, and a real image 36 of the plate 28 is formed via an optical system formed of a lens 30, a lens 32 and a half mirror 34 across vessels 12 existing under a skin surface 16 of a living body.

As the filter 23, a filter of a central wave length of 550 nm and a mean-width of 40 nm is used. As the plate 28, a photodiffusion plate is used, for example, a frost-type plate manufactured by Sigma Optical Materials Co., Ltd., Japan.

The real image 36 of the plate 28 including the vessels 12 is a detection region V. Reflected light from the region V is received by CCD 40 via the half mirror 34 and a lens 38.

The filter 23, diffuser 26, plate 28, lenses 30, 32 and 38, the half mirror 34 and CCD 40 are disposed within the probe 58. The tip 59 of the probe 58 closely contacts the skin surface 16 through a plastic or glass transparent plate 66, which enables a stable image to be captured without blurring.

An image signal output from each pixel of CCD 40 is processed on a video signal processor 46. The video signal processor 46 successively produces frames of images at a rate of one frame per 1/30 seconds. The produced frames of images are recorded one after another in a video recorder 50 (e.g., a laser disk recorder).

The analysis device 70 processes the captured image to analyze the blood within the vessel included in the detection region V. A commercially available personal computer may be used as the analysis device 70.

The analysis device 70 comprises trim device 71 for trimming the image output from the video recorder 50 for obtaining a necessary region and outputting the region, histogram producing device 72 for producing a histogram with respect to the intensity of the individual pixels in the trimmed region of the image, intensity detecting device 73 for detecting a intensity A as the intensity $I_B$ of the blood and a intensity B as the intensity $I_T$ of the living body tissue when the histogram of the intensity become maximum at the intensity A and B (A<B), diameter determination device 74 for determining the diameter D of the vessel included in the trimmed region of the image, hemoglobin concentration calculation device 75 for calculating the concentration of hemoglobin based on the detected intensity $I_B$ and $I_T$ and the determined diameter D of the vessel, and correction device 76 for correcting, if necessary, the calculated concentration of hemoglobin. Each image and histogram produced by the analysis device 70 are monitored on a monitor TV set 80.

Figure 2:
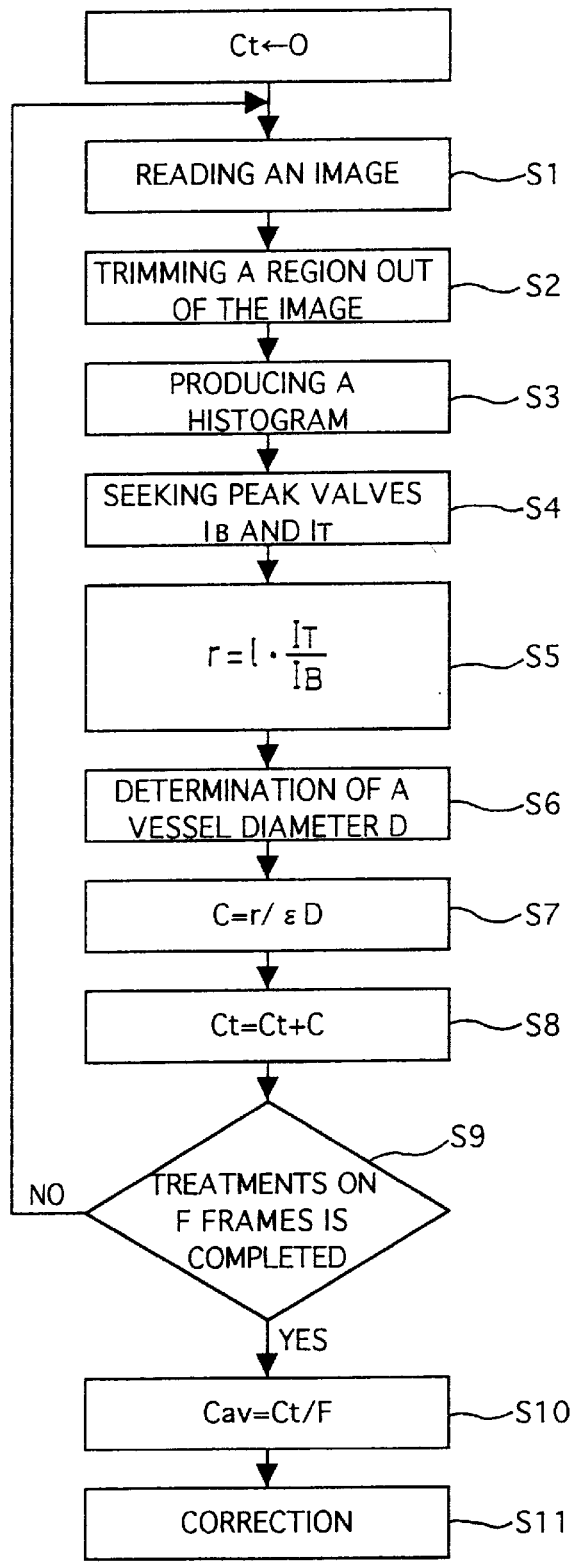
FIG. 2 is a flow chart showing an operational procedure according to embodiment 1.

A procedure for calculation of the concentration of hemoglobin using the analysis device 70 will hereafter be explained with reference to the flow chart shown in FIG. 2.

Here, the analysis device 70 reads and processes successively a plurality of frames or fields of images recorded in time sequence on the video recorder 50.

Figure 3:
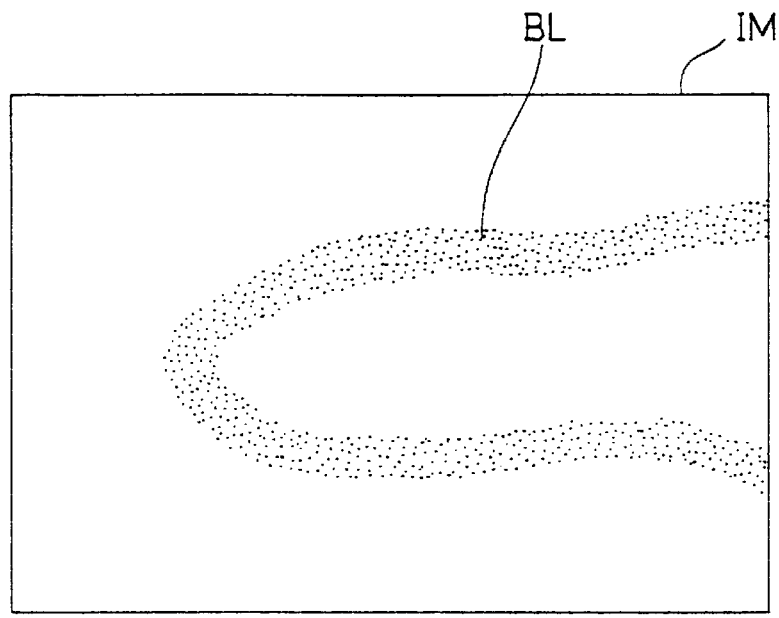
FIG. 3 is a view showing an example of an image captured according to embodiment 1.
Figure 4:
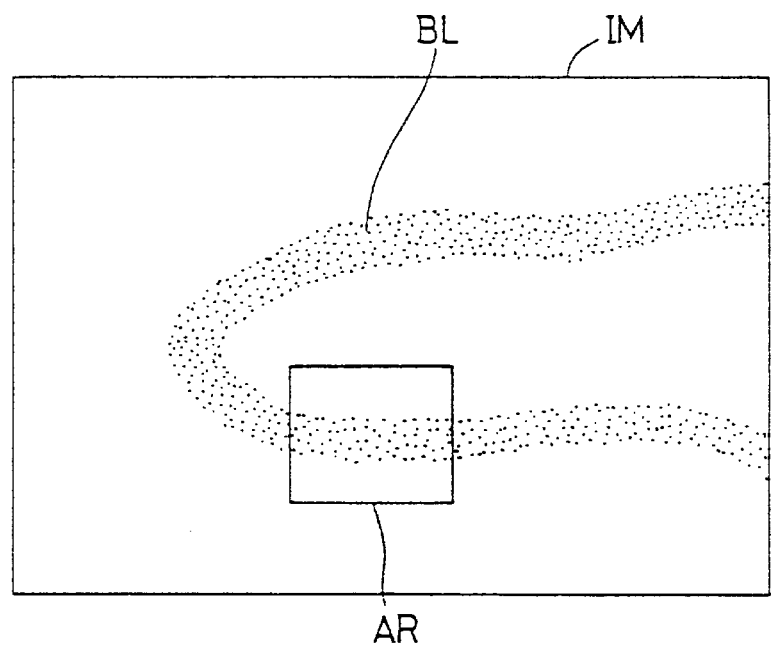
FIG. 4 is a view explaining the trimming of an image.

First, as shown in FIG. 3, a frame of an image IM including a vessel BL is read (step S1), and then, as shown in FIG. 4, a region AR (e.g., 100×100 pixels) including the vessel BL is trimmed out of the frame (step S2).

Figure 5:
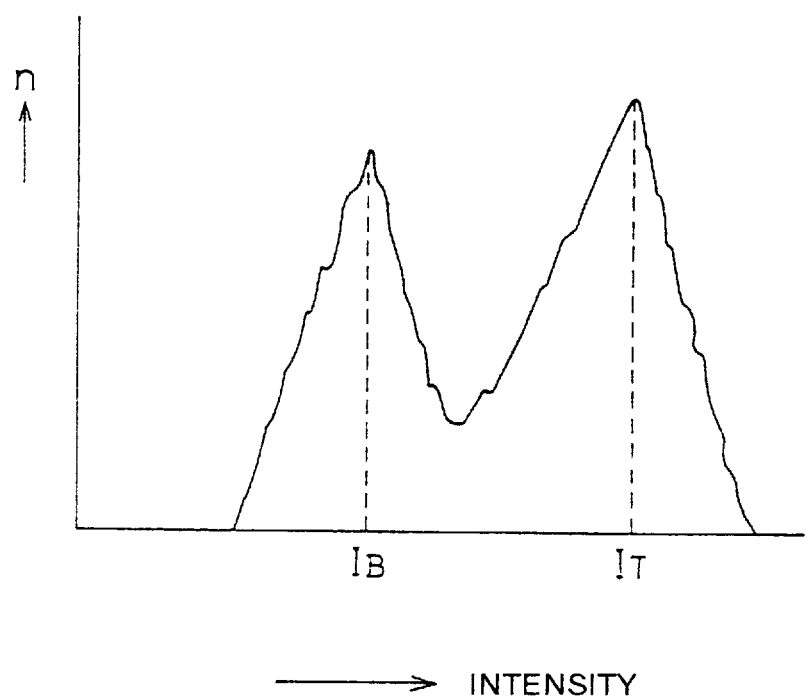
FIG. 5 is an exemplary histogram showing intensity distribution of captured images according to embodiment 1.

Then, as shown in FIG. 5, the histogram of n frequency is produced with respect to the intensity of pixels in the trimmed region AR (step S3), and, of the two intensity showing peak values, the lower intensity is detected as the intensity of the blood $I_B$ and the higher intensity is detected as the intensity of the living body tissue $I_T$ (step S4).

Next, $r=\log_a(I_T/I_B)$ is calculated (step S5), the diameter D of the vessel BL is calculated from the image, and C=r/εD is calculated (step S7), which is added to the already calculated Ct to obtain a new Ct (Step S8).

Steps S1 to S8 are repeated with respect to a plurality of frames, i.e., F frames (step S9), the obtained Ct is divided by F to obtain a mean value $C_{av}$ (step 10). The mean value $C_{av}$ obtained from an arteriole or venule is then converted with correction to the corresponding value of a medium-sized artery or vein or the main artery or vein to obtain the concentration of hemoglobin HGB (step S11). The correction is actually made based on an experimentally obtained correction function.

For 9 persons of HGB values of 14 (g/dl) to 18 (g/dl), the correlation between the HGB value X obtained on a blood cell counter and the HGB value Y calculated according to the present invention was examined. The obtained coefficient of correlation was 0.861, which proved that the HGB value Y obtained according to the present invention was of enough practical use.

Embodiment 2

Figure 6:
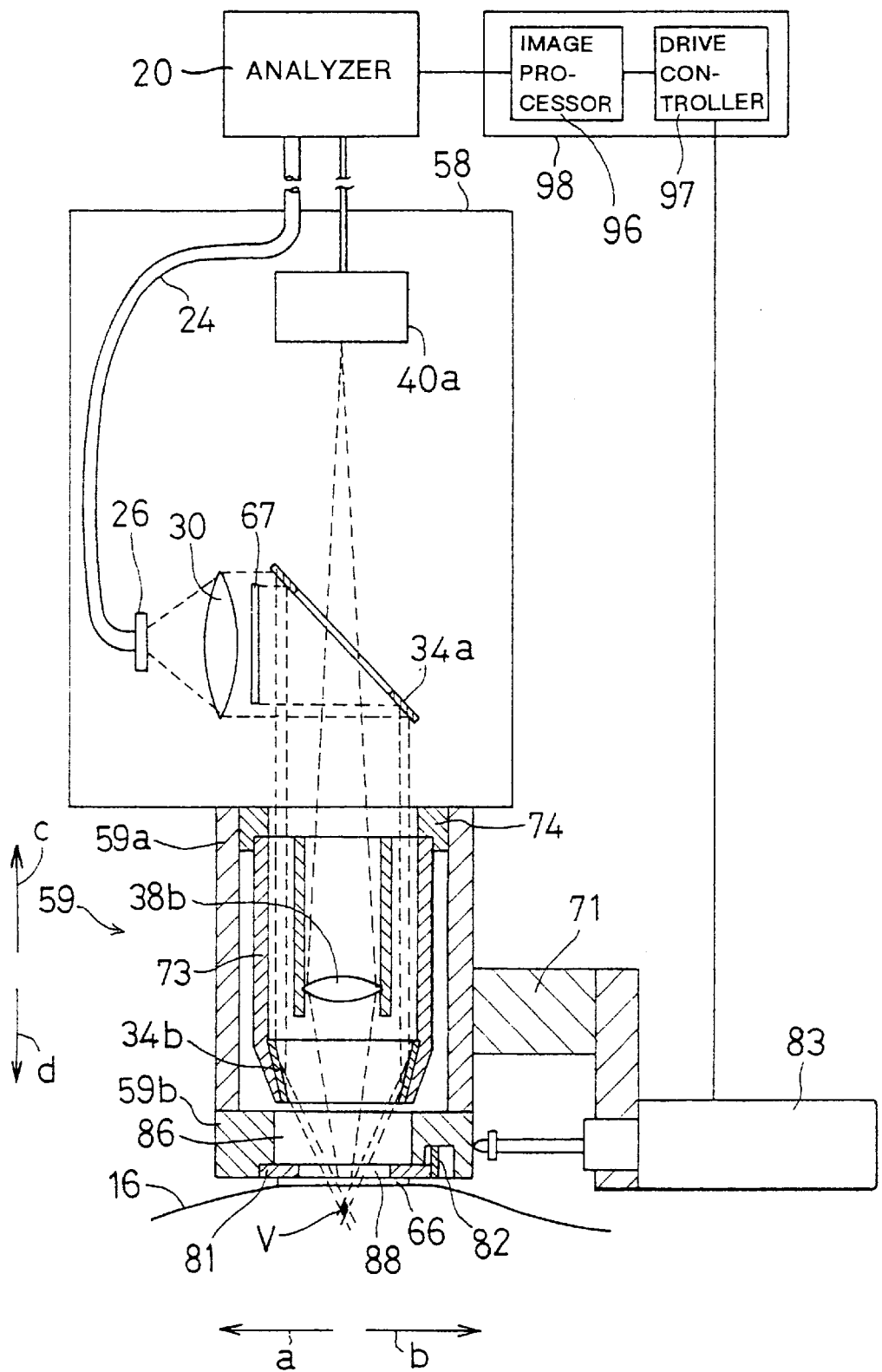
FIG. 6 is a view illustrating the structure of embodiment 2 of the present invention, the view showing an essential portion thereof.

FIG. 6 is a view illustrating an essential portion of embodiment 2 of the present invention. The same elements as in FIG. 1 are referred to with the same reference numerals. An analyzer 20 includes the light source 22, the video signal processor 46, the video recorder 50, and the analysis device 70 which are shown in FIG. 1. A light beam emitted by the light source within the analyzer 20 is directed into the probe 58 via the optical fiber 24 and illuminates the diffuser 26. The light beam is diffused by the diffuser 26 and converted into parallel light by a collimating lens 30.

The center of the parallel light beam is interrupted with a screen 67 and the periphery of the parallel light beam is emitted from the tip 59 of the probe via ring-like mirrors 34a and 34b. The light beam emitted from the tip 59 of the probe illuminates the detection region V including blood through a transparent plate 66 and a skin surface 16.

The light beam from the region V is received by a CCD 40a through the transparent plate 66 and an objective lens 38b. An image captured by CCD 40a is analyzed on the analyzer 20. The analyzer 20 analyzes and calculates blood components as described in Embodiment 1 (e.g, the intensity of transmitted or reflected light is obtained from the image for analyzing hemoglobin).

The non-invasive blood analyzer according to Embodiment 2 is characterized by irradiating the detection region with dark-field illumination so as to improve the contrast on a captured image.

Figure 14:
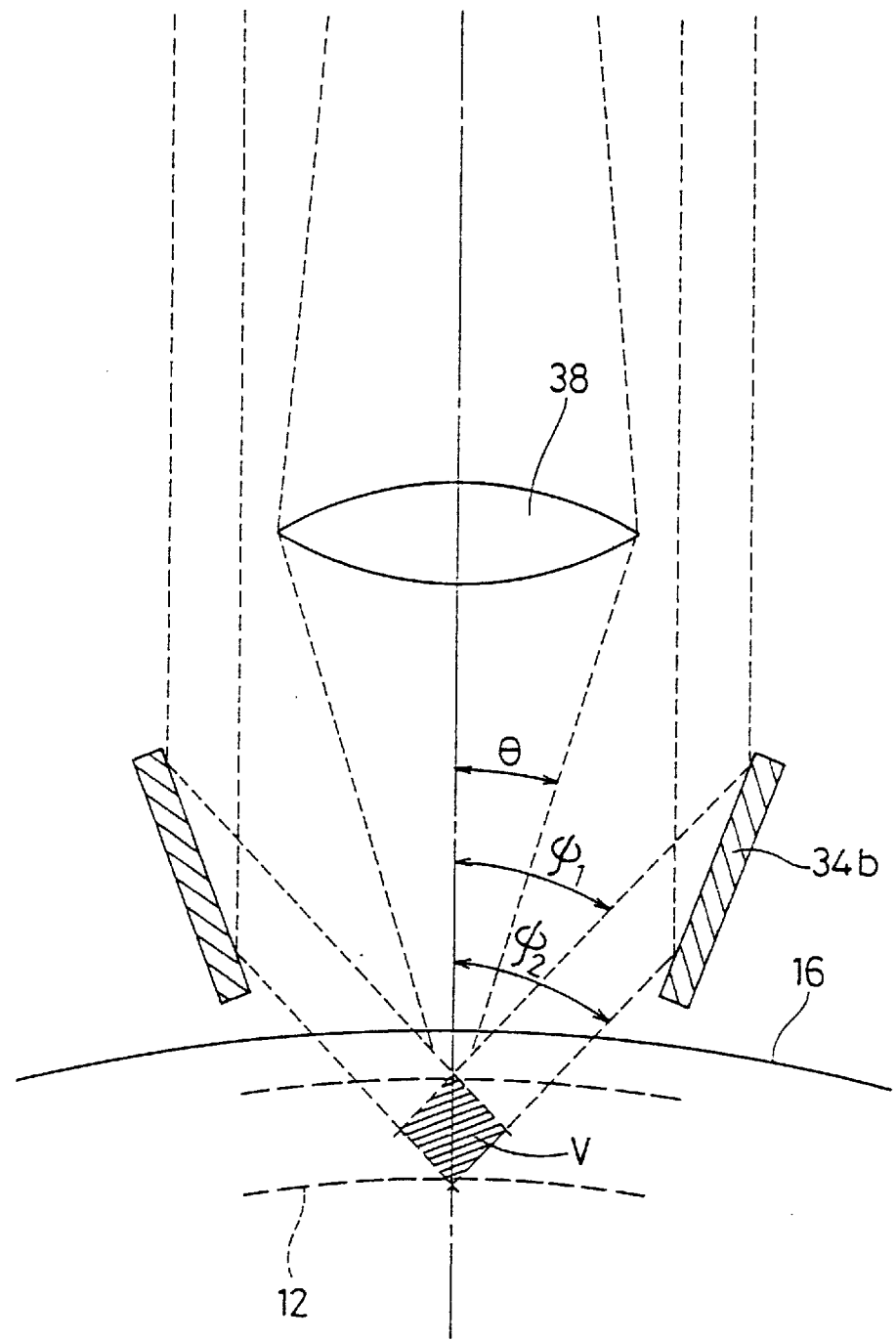
FIG. 14 illustrates the illumination according to embodiment 2.

The dark-field illumination defined here refers to an illumination mode by which the illumination light is directed to the detection region V from the outside of the objective lens 38, as shown in FIG. 14. In other words, the illumination light illuminates the detection region V at an angle $\phi 1$ or $\phi 2$ broader than an aperture angle θ of the objective lens 38b with respect to the detection region V. Consequently, since the illumination light reflected at the skin surface 16 is directed to the outside of the aperture angle θ of the objected lens 38b, thus failing to reach CCD 40a, the contrast on the image captured by CCD 40a is greatly improved.

In addition, each blood component has its own light absorption characteristics. For capturing an image of a blood component A with sharp contrast, a light may be employed having a wavelength for which the blood component A shows a large absorptivity.

The non-invasive blood analyzer of Embodiment 2 is also characterized by having a function to detect a desired vessel for the analysis and a function to keep the detected vessel at a predetermined position in an imaging field in spite of an outer disturbance such as a body move of a person under test.

Referring to FIGS. 6 to 9, the tip 59 of the probe 58 provides an external cylinder 59a extending from the probe 58, and a sliding board 59b slidably supported with linear sliders 80a and 80b at the end of the external cylinder 59a. The sliding board 59b can slide in the directions of arrows a and b. The sliding board 59b has on its front surface a support plate 81 provided with a transparent plate 66, the support plate 81 releasably fitted and urged with leaf springs 82 into engagement with the sliding board 59b. An internal cylinder 73 incorporates the objective lens 38b and the ring-like mirror 34b and is fixed to the probe 58 via a micro-motion element 74.

The focus of the CCD 40a is adjusted by moving the lens 38b in the direction of the optical axis (in the direction shown by arrow c or d) with the micro-motion element 74. As the micro-motion element 74, for example, an element with piezotrical element P-720/P-721 (manufactured by Physik Instrumente), or an element with an ultrasonic motor may be used, for example.

An L-shaped bracket 71 extends from the circumferential wall of the external cylinder 59a and supports a motor micrometer head 83. The motor micrometer head 83 has an output rod 84 whose tip abuts the side of the sliding board 59b.

The motor micrometer head 83 receives a signal from a controller having an image processor 96 and a drive controller 97 and moves the output rod 84 in the direction of the arrow a or b. As for the motor micrometer head, SOM-13 type device manufactured by Sigma Optical Materials Co., Ltd., Japan may be employed.

Figure 7:
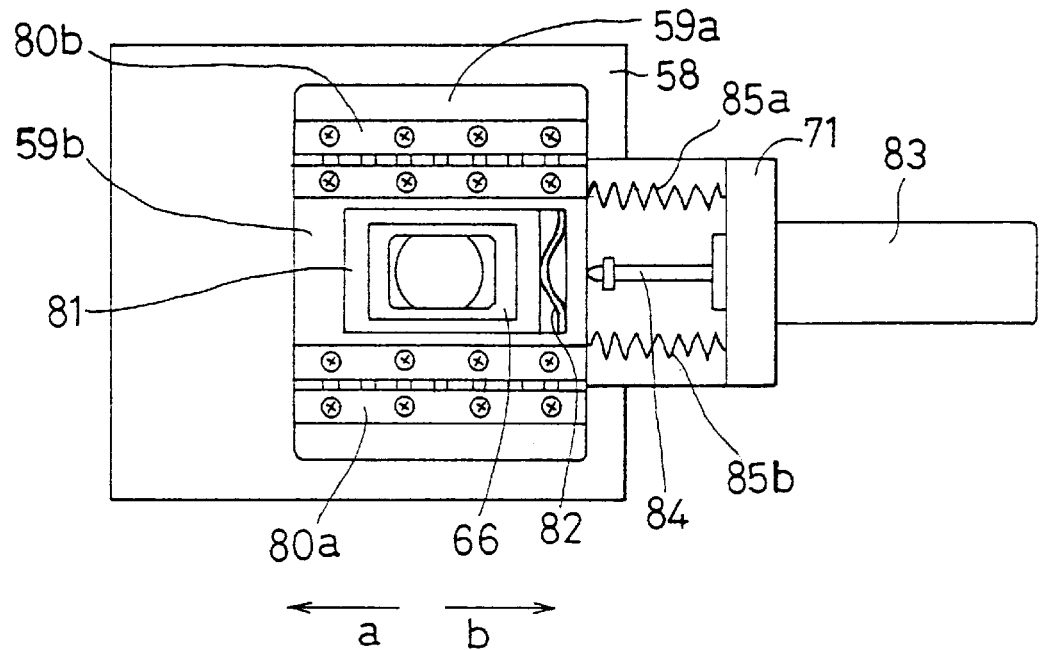
FIG. 7 is an elevational view of the essential portion according to embodiment 2.
Figure 8:
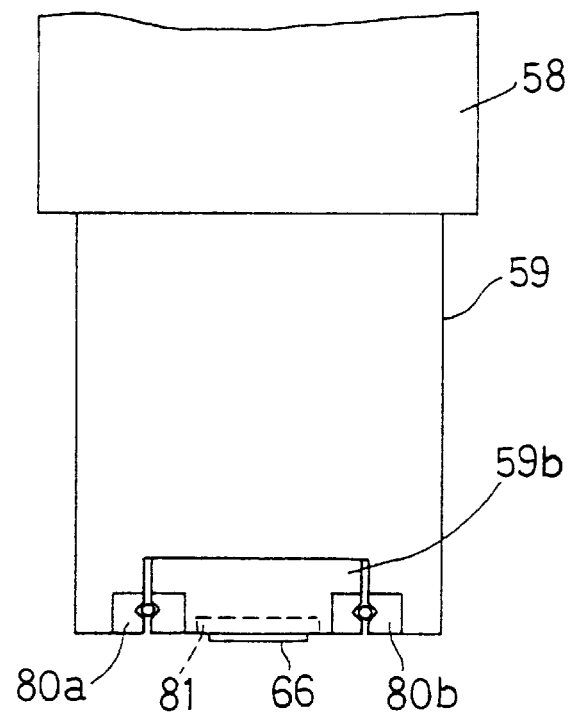
FIG. 8 is a side view of the essential portion according to embodiment 2.
Figure 9:
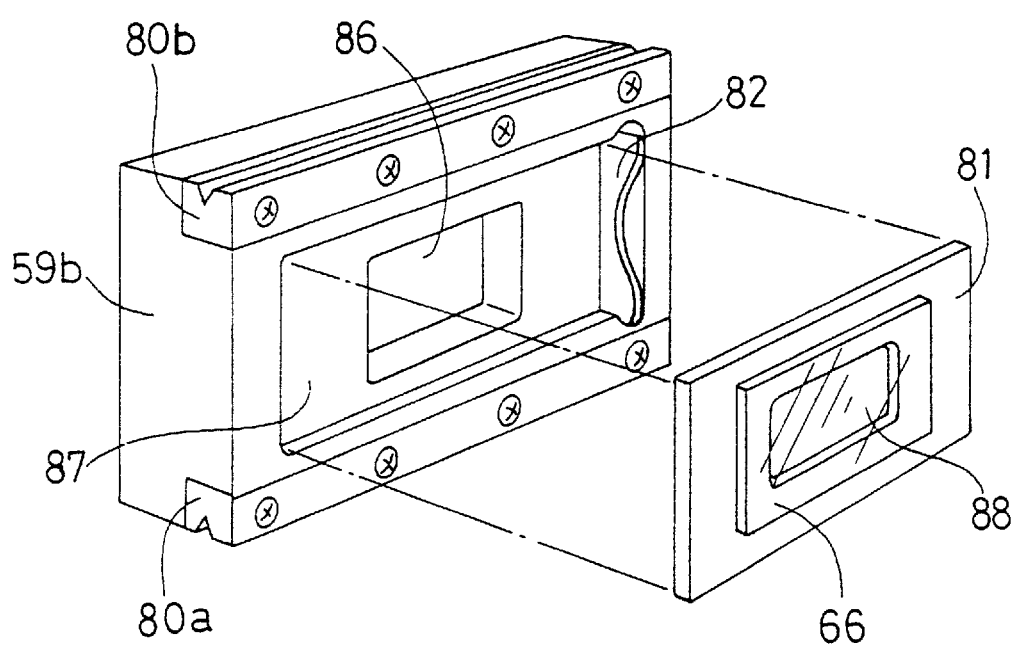
FIG. 9 is a perspective view of the essential portion according to embodiment 2.

FIG. 7 is an elevational view of the tip 59 of the probe, FIG. 8 is a side view thereof and FIG. 9 is an exploded perspective view of the sliding board 59b. As shown in FIG. 7, the sliding board 59b and bracket 71 are interconnected with coiled springs 85a and 85b and the sliding board 59b is biased in the direction of the arrow b.

The sliding board 59b, as shown in FIG. 9, has an opening 86 and a recess 87. The support plate 81 is fit in the recess 87 and releasably fixed with the leaf springs 82. The support plate 81 has an opening 88 which is covered by the transparent plate 66 adhered to the support plate 81 beforehand, for example, with an adhesive agent or tape. A glass plate, a plastic film, or the like may be used as the transparent plate 66. The support board 81 together with the transparent plate 66 is exchangeably attached on the tip 59 of the probe 58 for hygienic purposes (e.g., for protecting subjects from infection of diseases).

Figure 10:
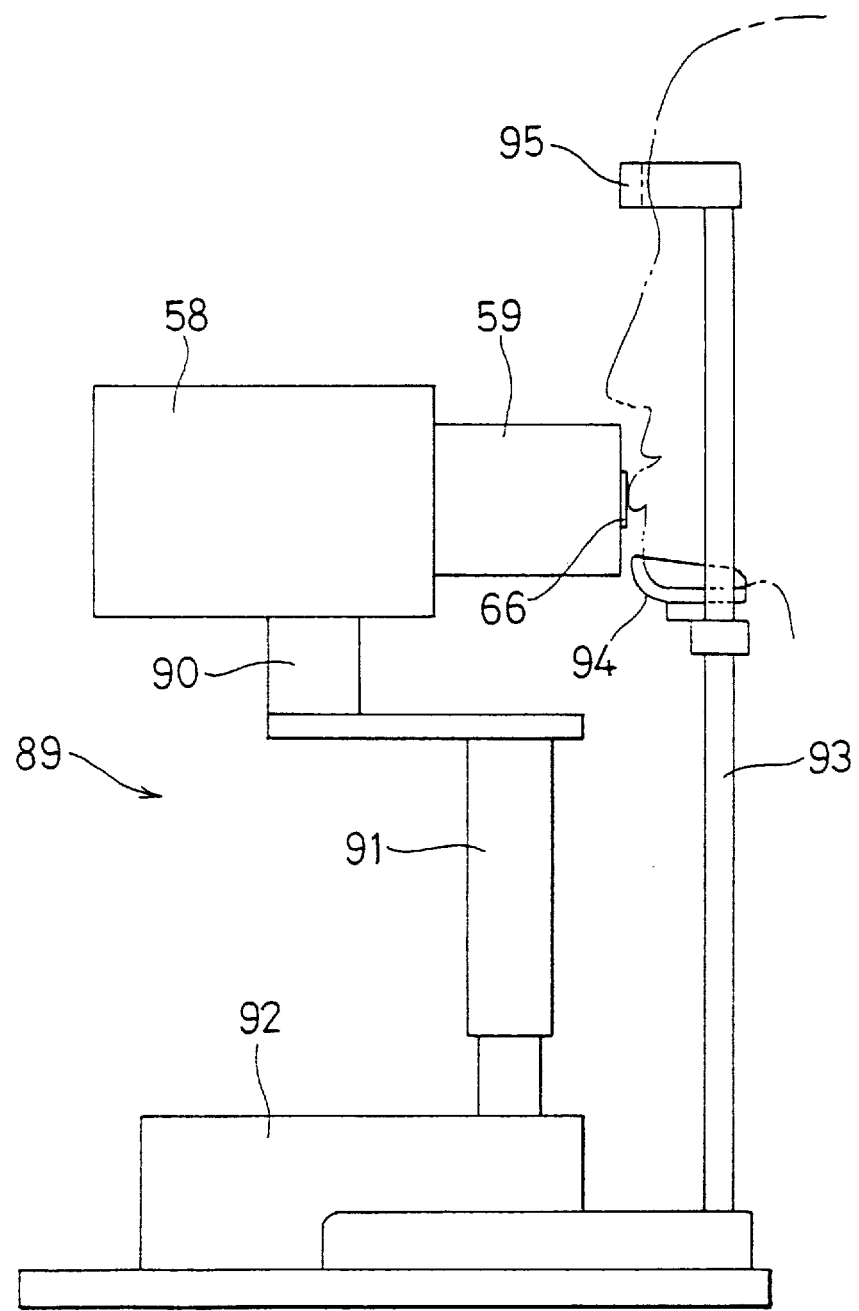
FIG. 10 is a view illustrating the structure of embodiment 2.

The probe 58 is mounted on a manipulator 89 shown in FIG. 10. The manipulator 89 has an angle control portion 90 for controlling the angle of the probe 58, a height control portion 91 for controlling the vertical position of the probe 58 and a position control portion 92 for controlling the position of the probe 58 in horizontal directions, i.e., right, left, front and back. The manipulator 89 also has a stand 93 for supporting the head of a subject provided with a chin support 94 for supporting the chin of the subject and a head fixer for fixing the position of the head.

As shown in FIG. 10, when a subject places the head on the stand 93, the probe 58 is adjusted to take such a horizontal and vertical position that the transparent plate of the tip 59 of the probe is closely contacted with a lip of the subject with appropriate pressure.

In this state, when the output rod 84 is driven by the motor micrometer head 83 shown in FIG. 6, the transparent plate 66 contacted with the lip moves vertically to the sheet of paper in FIG. 10. As the transparent plate 66 moves, soft tissue of the lip moves with the transparent plate 66 by the friction caused on the contacting faces, and thus the region imaged by the probe 58 is shifted.

Since there are capillaries, arterioles and venules existing together at intervals of several tens of microns in the lip, only a move by several tens of microns to several milmeters of the transparent plate 66 allows a desired vessel to be detected and put in the imaging field. Such a move is so small that the blood flow in the lip may not be disturbed by the move of the transparent plate 66.

Figure 11:
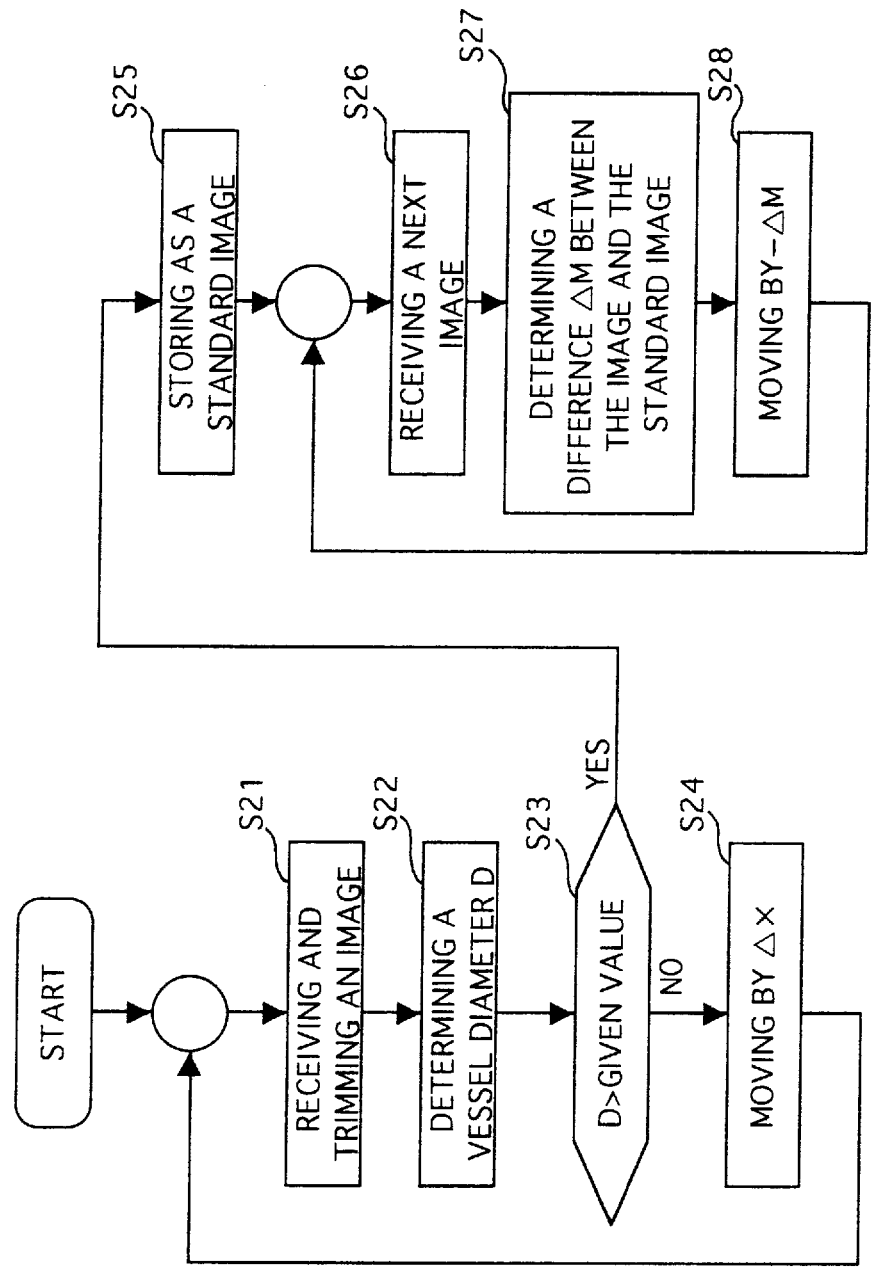
FIG. 11 is a flow chart showing an operational procedure according to embodiment 2.

Now the operation of the controller 98 for automatic control of the movement of the transparent plate 66, that is, the image processor 96 and the drive controller 97, will hereafter be explained with reference to the flow chart shown in FIG. 11.

Figure 12:
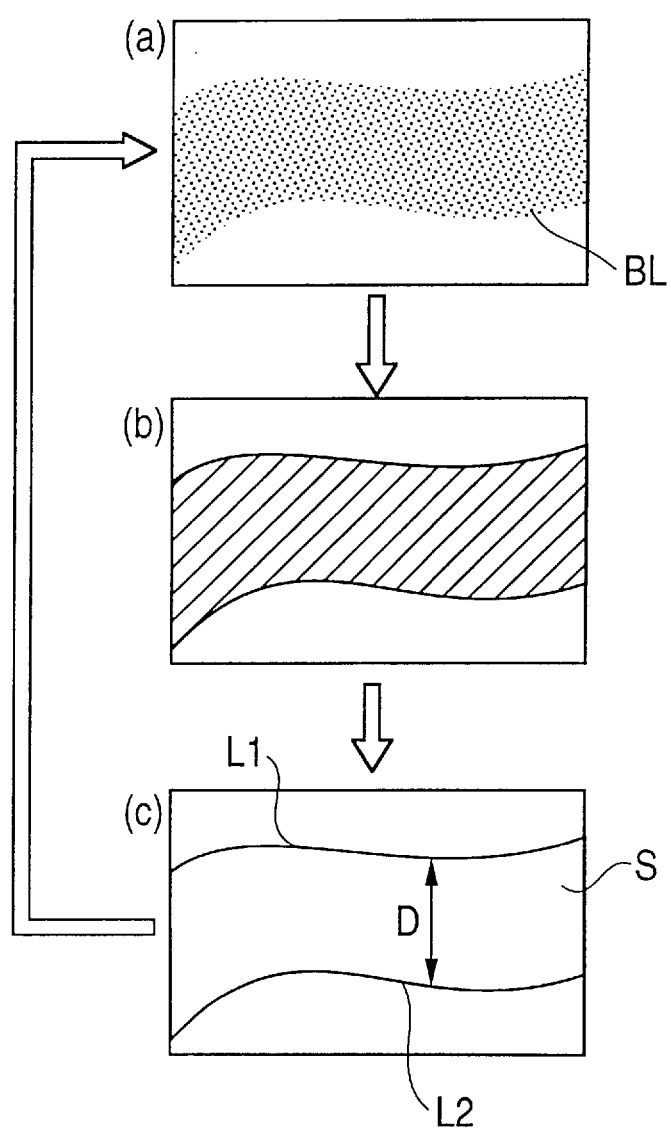
FIG. 12(a) to 12(c) illustrate how to calculate the diameter of a vessel according to embodiment 2.

When CCD 40a (FIG. 6) captures an image, the image processor 96 receives a frame of the image including a vessel BL and trims the frame with a predetermined region as shown in FIG. 12(a) (step S21). Then the image processor 96 determines the diameter D of the vessel BL (step S22).

In this step 22, for example, the outline of the vessel BL is clarified by binarizing the image as shown in FIG. 12(b), the edges are extracted as shown in the FIG. 12(c), and then the length of individual edges L1, L2 and the mean length La are calculated. Also the area S of the vessel BL is calculated from the number of pixels representing the vessel BL and the diameter D=S/La is calculated.

When the calculated diameter D is smaller than a predetermined value (e.g., 20 microns) (step S23), the image processor 96 outputs a signal to the drive controller 97, which, on receipt of the signal, drives the motor micrometer head 83 for moving the transparent plate 66 by a distanced ΔX (e.g., 10 microns) in the direction of the arrow a or b through the output rod 84 (step S24).

The controller 98 repeated the steps S21 to S24 until the image processor 96 finds out a vessel of a diameter D larger than the predetermined value in the step S23. On finding such a vessel, the controller stops detecting a vessel and stores the frame of the image of the detected vessel as a standard image in an image memory (step S25).

Figure 13:
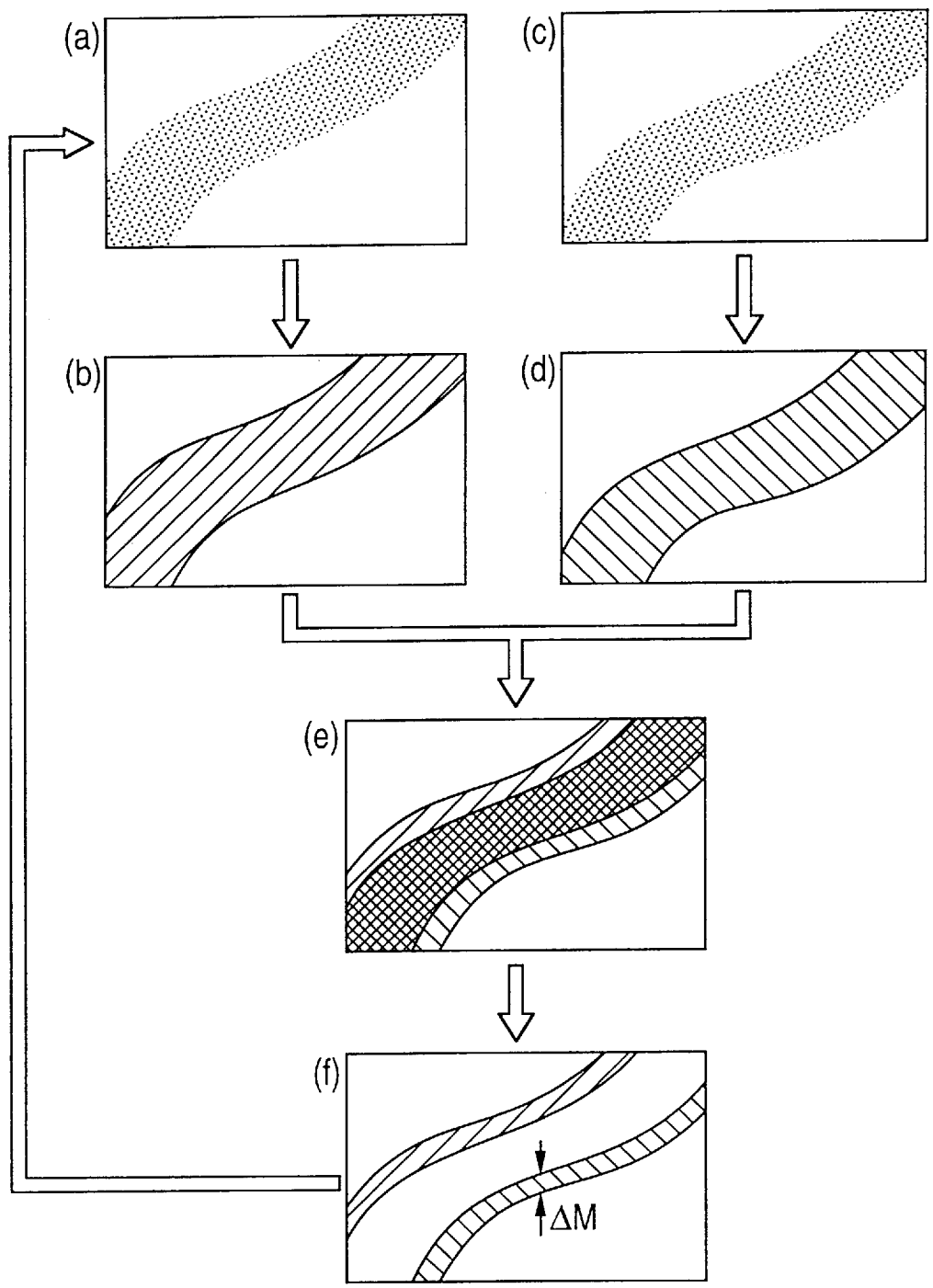
FIG. 13(a) to 13(f) illustrate how to compensate a change in position of a vessel.

CCD 40a carries out a next image capturing and, when CCD 40a obtains a frame of an image as shown in FIG. 13(c), the image processor 96 stores the captured image in the image memory (step S26).

Then the image processor 96 calculates a difference ΔM between the standard image (step 27) and the captured image shown in FIG. 13(c).

In this step 27, for example, the standard image and captured image are binarized (digitized) as shown respectively in FIGS. 13(b) and (d), and the binarized images are compared as shown in FIG. 13(e) for calculation of the difference ΔM therebetween as shown in FIG. 13(f).

When the difference ΔM is calculated, the image processor 96 outputs a signal to the drive controller 97, which, on receipt of the signal, drives the motor micrometer head 83 for moving the transparent plate 66 in the direction of the arrow a or b through the output rod 84 (step S24) so that the difference ΔM is reduced to zero (step S28).

According to Embodiment 2, a vessel having a desired diameter can be automatically detected and, in addition, a change in position of the detected vessel on captured images, if caused by a body move or other external disturbance, can be compensated automatically.

As the image processor 96, a microcomputer comprising ROM, RAM (including an image memory) and CPU may be used, for example and, as the drive controller 97, a conventional servo control circuit driving a DC servomotor incorporated in the motor micrometer head 83 can be used, for example.

According to the present invention, since the region to be imaged can be shifted by the drive control device, a desired vessel is detected quickly and easily, and the change in position of the vessel is automatically compensated. When the transparent plate is moved by the drive control device, tissue including vessels near skin of a human body moves with the move of the transparent plate. Thus a vessel to be imaged of a desired diameter can be detected and the difference in position of the vessel can be minimized.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A non-invasive blood analyzer comprising:
   light application device for illuminating a detection region including a blood vessel having blood flowing therethrough, the detection region being under skin of a part of a living body;
   image capturing device for capturing an image of the illuminated detection region;
   analysis device for processing the captured image and analyzing at least a component of the blood in the blood vessel in the detection region;
   a transparent plate contacting the skin, the light application device illuminating the detection region through the transparent plate and the image capturing device capturing the image of the detection region through the transparent plate;
   support device for supporting the transparent plate; and
   drive control device for driving the support device to move the transparent plate in order to adjust the detection region.

2. The non-invasive blood analyzer of claim 1, wherein the analysis means is further for determining a diameter of the blood vessel and for comparing the diameter with a predetermined value, and wherein the drive control device controls the support device to move the transparent plate by a predetermined distance when the diameter is smaller than the predetermined value.

3. The non-invasive blood analyzer of claim 1, wherein the analysis means is further for processing the image and for determining a difference in position of repeatedly captured images with respect to the blood vessel, and wherein the drive control device controls the support device to move the transparent plate so as to minimize the determined difference.

4. The non-invasive blood analyzer of claim 3, further comprising a memory for storing at least one captured image.

5. The non-invasive blood analyzer of claim 4, wherein the memory stores an initially captured image as a reference image and the analysis device compares a position of a blood vessel in the reference image with a position of the blood vessel of a next-captured image, captured after the support device has moved the transparent plate by a predetermined distance.

6. The non-invasive blood analyzer of claim 5, wherein the image capturing device captures an image of a blood vessel after the support device moves the transparent plate so as to minimize the determined distance, the analysis device analyzing a component of the blood in the blood vessel in the last captured image.

7. The non-invasive blood analyzer of claim 1, wherein the support means includes a support plate, having an opening therein, for receiving the transparent plate.

8. The non-invasive blood analyzer of claim 1, wherein the support means includes a support plate, having and opening therein, for receiving the transparent plate; a sliding board to which the support plate is exchangeably attached; and a support member for slidably supporting the sliding board.

9. The non-invasive blood analyzer of claim 1, wherein the support means includes a support member for slidably supporting the transparent plate.

10. The non-invasive blood analyzer of claim 9, wherein the drive control means includes bias means for biasing the transparent plate in a sliding direction and pressing means for moving the transparent plate.

11. The non-invasive blood analyzer of claim 10, wherein the bias means includes a spring and the pressing device includes a rod and a motor for moving the rod.

12. The non-invasive blood analyzer of claim 1, wherein the transparent plate is made of either glass or a plastic sheet.

13. The non-invasive blood analyzer of claim 1, wherein the support device includes a support member for slidably supporting the transparent plate and fixing device for fixing the support member on the living body.

14. The non-invasive blood analyzer of claim 1, further comprising a memory for storing the captured image.

15. A method of non-invasively analyzing blood, comprising the steps of:
   illuminating a detection region through a movable transparent plate, the detection region being under skin of a part of a living body and including a blood vessel having blood flowing therethrough;
   capturing an image of the detection region illuminated through the transparent plate;
   analyzing a component of the blood in the blood vessel in the detection region; and
   driving a support, supporting the transparent plate, with a driving device to move the transparent plate in order to adjust the detection region.

16. The method of non-invasively analyzing blood of claim 15, further comprising the steps of:
   successively capturing images of the detection region under the skin shifted by the driving device;
   comparing a diameter of each captured blood vessel image with a predetermined value; and
   analyzing a component of the blood contained in the blood vessel when the captured blood vessel image is larger than the predetermined value in diameter.

17. The method of non-invasively analyzing blood of claim 15, further comprising the steps of:
   capturing at least two images of the blood vessel;
   determining a difference in position between the at least two captured images with respect to the blood vessel;
   moving the transparent plate by a distance such that the determined difference is minimized; and
   capturing a next image of the blood vessel after the transparent plate has been moved.

18. A non-invasive blood analyzer comprising:
   a light source for illuminating a detection region through a movable transparent device, the detection region being under skin of a part of a living body and including a blood vessel;
   a light capturing device for capturing an image of the detection region illuminated through the transparent device;

an analyzer for analyzing the captured image and determining whether or not a captured blood vessel image is larger in diameter than a predetermined value;

memory for storing the captured image if the diameter of the image of the captured blood vessel is determined to be larger than the predetermined value; and a controller for controlling the transparent device to move by a predetermined distance when the diameter of the image of the captured blood vessel is not determined to be larger than the predetermined value.

19. The non-invasive blood analyzer of claim 18, wherein the light capturing device captures a next image of the detection region illuminated through the transparent device subsequent to the controller controlling the transparent device to move by a predetermined distance, the analyzer determines a difference between the stored captured image and the captured image with respect to the blood vessel, the controller controls the transparent device to move so as to minimize the difference, and the light capturing device thereafter captures a final image of the blood vessel.

* * * * *